(12) United States Patent
Groezinger et al.

(10) Patent No.: US 7,482,606 B2
(45) Date of Patent: Jan. 27, 2009

(54) APPARATUS AND METHOD FOR COMPENSATION OF MOVEMENTS OF A TARGET VOLUME DURING ION BEAM IRRADIATION

(75) Inventors: Sven Oliver Groezinger, Bensheim (DE); Thomas Haberer, Frankfurt (DE); Wolfgang Ott, Dossenheim (DE); Klaus Poppensieker, Darmstadt (DE)

(73) Assignee: Gesellschaft fuer Schwerionenforschung mbH, Darmstadt (DE)

( * ) Notice: Subject to any disclaimer, the term of this patent is extended or adjusted under 35 U.S.C. 154(b) by 509 days.

(21) Appl. No.: 11/148,808

(22) Filed: Jun. 9, 2005

(65) Prior Publication Data

US 2006/0033042 A1   Feb. 16, 2006

(30) Foreign Application Priority Data

Jun. 9, 2004   (DE)   ......................   10 2004 028 035

(51) Int. Cl.
*A61N 5/00*   (2006.01)
*G21G 5/00*   (2006.01)
(52) U.S. Cl. .............. 250/492.3; 250/492.1; 250/505.1; 378/65; 378/162; 378/163; 378/98.5; 600/439
(58) Field of Classification Search .............. 250/492.3, 250/492.1, 505.1; 378/65, 162, 163, 98.5; 600/439
See application file for complete search history.

(56) References Cited

U.S. PATENT DOCUMENTS 5,260,581 A   11/1993   Lesyna et al.

(Continued)

FOREIGN PATENT DOCUMENTS

DE   199 07 064 A   8/2000

(Continued)

OTHER PUBLICATIONS

Li Qiang, Groezinger Sven Oliver, Haberer Thomas, Rietzel Eike, Kraft Gerhard, "Online compensation for target motion with scanned particle beams: simulation environment", Physics in Medicine and Biology, vol. 49, pp. 3024-3046 (Jul. 21, 2004).*

(Continued)

*Primary Examiner*—David A. Vanore
*Assistant Examiner*—Meenakshi S Sahu
(74) *Attorney, Agent, or Firm*—Frommer Lawrence & Haug LLP; Ronald R. Santucci

(57) ABSTRACT

The invention relates to an apparatus and method for compensation of three-dimensional movements of a target volume (1) during ion beam irradiation. For the purpose, the apparatus comprises a position location and tracking system (4) for detecting the movements and a depth modulator (6) for modifying the depth of penetration of the ion beam. For the purpose of compensation, the movements are divided vectorially into a transverse component and a longitudinal component. The transverse component is compensated from irradiation point to irradiation point using the raster scanning apparatus (3) and the longitudinal component is compensated from irradiation point to irradiation point using the depth modulator (6) by means of the fact that, in addition to the change in the location of the target volume, the change in the structure of healthy tissue covering the target volume is, in the preliminaries to irradiation, detected and modelled and stored in the form of a look-up table in a memory of a movement measurement, control and read-out module SAMB and compared with the actual values during irradiation.

38 Claims, 9 Drawing Sheets

U.S. PATENT DOCUMENTS

| | | | |
|---|---|---|---|
| 5,895,926 | A | 4/1999 | Britton et al. |
| 6,118,848 | A * | 9/2000 | Reiffel ........................ 378/65 |
| 6,509,573 | B1 | 1/2003 | Badura et al. |
| 6,683,318 | B1 | 1/2004 | Haberer et al. |
| 6,710,362 | B2 * | 3/2004 | Kraft et al. ............... 250/492.3 |
| 2003/0136924 | A1 * | 7/2003 | Kraft et al. ............... 250/492.3 |

FOREIGN PATENT DOCUMENTS

| | | |
|---|---|---|
| DE | 100 31 074 A1 | 1/2002 |
| DE | 100 57 824 A1 | 6/2002 |
| EP | 1 045 399 A | 10/2000 |
| EP | 1 454 656 A | 9/2004 |

OTHER PUBLICATIONS

Groezinger, Sven Oliver, "Chapter 5 A Motion Compensation System for Heavy Ion Therapy" *Volume Conformal Irradiation of Moving Target Volumes with Scanned Ion Beams*, pp. 65-76.

Brusasco, C. et al.: "A dosimetry system for fast measurement of 3D depth-dose profiles in charged-particle tumor therapy with scanning techniques", *Nuclear Instruments and Methods in Physics Research B*, 168(2000) pp. 578-592.

Groezinger, Sven Oliver, "Chapter 5 A Motion Compensation System for Heavy Ion Therapy" *Volume Conformal Irradiation of Moving Target Volumes with Scanned Ion Beams*, pp. 65-76.

Brusasco, C. et al.: "A dosimetry system for fast measurement of 3D depth-dose profiles in charged-particle tumor therapy with scanning techniques", *Nuclear Instruments and Methods in Physics Research B*, 168(2000) pp. 578-592.

Pedroni, Eros et al.: "The PSI Gantry 2: a second generation proton scanning gentry", *Z. Med. Phys.*, 14 (2004), pp. 25-34.

Bar, R. et al.: "Status and Controls Requirements of the Planned Heavy Ion Tumor Therapy Accelerator Facility Hicat".

Search Report issued by European Patent Office for European Application EP 05010450 dated Sep. 7, 2005.

* cited by examiner

APPARATUS AND METHOD FOR COMPENSATION OF MOVEMENTS OF A TARGET VOLUME DURING ION BEAM IRRADIATION This application claims priority benefits of German Patent Application No. 10 2004 028 035.5 filed Jun. 9, 2004.

The present invention relates to an apparatus for compensation of three-dimensional movements of a target volume on a patient couch during ion beam irradiation using, especially, a raster scanning apparatus. This apparatus comprises a position location and tracking system which detects the three-dimensional movements of the target volume longitudinally and transversely with respect to the ion beam. The apparatus further comprises a depth modulator, by means of which the depth of penetration of the ion beam can be re-adjusted. Furthermore, in a development, the apparatus is in operative connection with the raster scanning apparatus, which makes possible transverse deflection of the ion beam in fractions of milliseconds.

An apparatus of such a kind is known from joint consideration of the publications DE 100 31 074 A1 and EP 99 107 127, in which the principle of a method for precision irradiation of moving target volumes using the ion raster scanning method is also presented. The method described requires dynamic correction of the transverse and longitudinal irradiation parameters in irradiation run time.

The transverse correction is based on the raster scanning method and is described in the publication EP 99 107 127. Accordingly, using the raster scanning method, the settings in the transverse direction relative to the ion beam can be changed and thereby corrected from irradiation point to irradiation point. Because of the fact that an intensity control is also provided for the raster scanning method, this also makes it possible to modify the longitudinal irradiation parameters of a previously determined desired position. However, although the transverse modifications and corrections can be made in fractions of milliseconds, the longitudinal settings can be changed only in synchronicity with the cycle of the particle accelerator and, as a result, very slowly. The associated problem relating to the depth of penetration of the ion beam into tissue is illustrated in FIG. 1.

FIG. 1 shows the consequences that changes in the consistency of the structure of healthy tissue covering the target volume in the upstream direction of the beam have on distribution of the dose in the case of photon irradiation (curves a and b) compared to ion irradiation (curves c and d), the depth of penetration w being plotted against the abscissa and the ion dose absorbed by the tissue being plotted against the ordinate. In the event of three-dimensional movement of the body of a patient on a patient couch, it is not only the location of the patient and, as a result, the location of the target volume transversely and longitudinally relative to the ion beam that changes, but also the composition, density, thickness and consistency of the healthy tissue arranged in the direction of the beam upstream of the target volume, which results, in the case of photon irradiation, in curve b (during or after movement) differing from curve a (before movement) in terms of dose distribution.

In the case of ion irradiation, the consequences are much more serious, as comparison of curves c (before movement) and d (during or after movement) in FIG. 1 shows, because in the case of ion irradiation the dose distribution does not tail off exponentially along with the depth of penetration as it does in the case of photon irradiation but rather there is a dose escalation which can, because of the change in the covering tissue, be displaced, for example by the difference in depth of penetration $\Delta w$, in the event of movement, consequently missing the planned volume element of the target volume.

The distribution of the dose administered by ion irradiation is therefore, in contrast to photons, extremely sensitive to changes in the longitudinal direction, for example in the event of changes in density, in the healthy tissue through which the beam passes. Such changes occur, for example in the course of organ movement due to breathing, on a shorter time scale than the accelerator cycle which governs the speed with which the conventional raster scanning method could react. This means that correction, including correction of depths of penetration, cannot exactly follow changes resulting from movement of the patient in a short time span from irradiation position to irradiation position using the conventional raster scanning method. Detection of the longitudinal displacement of the target volume, in the event of patient movement, solely by means of precision video cameras, as is known from the publication DE 100 31 074 A1, does not allow exact beam modification or correction, even if that modification could be carried out from beam position to beam position on the basis of the apparatus disclosed therein for the shift in the target volume.

The intensity-modulated raster scanning method allows irradiation of deep-lying tumours with. extremely high geometric precision, albeit relatively slowly. However, the success of therapy is, in the case of beam therapy, dependent on the dose in the target volume, that dose generally being limited by the doses that are acceptable in the surrounding tissue. Compared to conventional photon irradiation, the geometric precision of the intensity-modulated raster scanning method makes it possible, in many cases, to obtain a dose escalation in the target volume, as shown in FIG. 1. In order to be able to utilise that precision, however, the relative location, in terms of position, of the target volume must, at all times during irradiation, coincide with the case assumed in an irradiation plan. The routinely used fixing of the target region does not provide sufficient accuracy in all cases, for example in the thoracic region. Any remaining change in length or displacement of the volume to be irradiated relative to the reference position for the irradiation plan results in incorrect positioning and, therefore, in an incorrect dose of ions. Accordingly, the number of ions actually administered per volume no longer agrees with the planned distribution, that is to say the homogeneity and geometry of dose distribution changes and the success of therapy is jeopardised as a result.

This problem is illustrated by FIG. 2, which shows the relative dose homogeneity for a statically fixed target volume (curve e) and for a target volume of changed location (curve f), in dependence upon the depth of penetration w. Even in the case of a static or fixed target volume, the dose homogeneity decreases with increasing depth of penetration w because of scatter and absorption mechanisms of the ion beam in the tissue. However, when the target volume has a static, that is to say fixed, location, that decrease is not more than 10% (curve e, FIG. 2) of the dose introduced. In the event of movement of the target volume, however, considerable longitudinal changes in depth of penetration can occur, as already shown in FIG. 1, so that the relative dose homogeneity can, as shown in FIG. 2, deteriorate by up to 60% (curve f, FIG. 2) if compensation is not carried out.

The problem of the invention is to provide an apparatus and a method for compensation of movements of a target volume during ion beam irradiation which overcome the problems described above and which improve the precision of irradiation of a target volume.

The problem is solved by the subject-matter of the independent claims. Advantageous developments of the invention will be found in the dependent claims.

In accordance with the invention, an apparatus and a method are provided for compensation of three-dimensional movements of a target volume on a patient couch during ion beam irradiation using a raster scanning apparatus. For the purpose, the compensation apparatus comprises a position location and tracking system, which detects the three-dimensional movements of the target volume longitudinally and transversely relative to the ion beam and which in the process is in operative connection with a movement measurement, control and read-out module SAMB. The compensation apparatus also comprises a depth modulator which is in operative connection with the movement measurement, control and read-out module SAMB for changing the depth of penetration w of the ion beam. In addition, the raster scanning apparatus, as part of the apparatus which deflects the ion beam transversely, is in operative connection with a location measurement, control and read-out module SAMO for changing excursion of the beam in a transverse direction.

For the purpose, the movement measurement, control and read-out module SAMB comprises a microprocessor having a memory. The memory contains data of a model of a structure of the healthy tissue which covers the target volume in the upstream direction of the beam. The microprocessor additionally comprises computational components which break down the detected movements of the target volume vectorially into longitudinal and transverse components. The computational components also compare the longitudinal components against the stored model for correction of the depth of penetration of the ion beam.

The data of a model in the memory are preferably derived from ultrasound sections or X-ray images of the healthy covering tissue over the target volume. Both X-ray investigations and also ultrasound investigations in the preliminaries to ion irradiation have the advantage that they are capable of exactly representing the healthy covering tissue over the target volume both in terms of its thickness and also in terms of its composition, its consistency and its density. As a result, the precision of compensation of longitudinal deviations can be carried out much more precisely than in the case of conventional apparatuses and methods. In addition, the validity of the model can be continuously ensured by further measurements using X-ray detection devices and/or ultrasound detection devices.

In addition, this apparatus has the advantage that, on the basis of the detected change in the location and position of the current target volume at the moment of irradiation, it is possible to determine a three-dimensional correction vector for the radiological position of the volume element in question and, by compensating for the disruptive movement by means of appropriately directed displacement of the therapy beam, it is ensured that the number of ions optimised in the preliminaries to irradiation in accordance with an irradiation plan is delivered to the volume element in question. To compensate for movement of the target region during irradiation, the therapy beam is re-adjusted in all three spatial directions. Dividing the compensation into a transverse and a longitudinal component allows re-adjustment by means of the raster scanning apparatus and by means of a depth modulator.

In the event that the target volume, because of its anatomical arrangement, does not move despite the fact that movements of the patient result in changes in the healthy tissue through which the beam passes, only longitudinal compensation is necessary; accordingly, the energy of the ion beam has to be modified in line with the movement so that in all cases the range of the ion beam is altered so that interaction with the target volume element is ensured. This is also the case when, for example, beam re-adjustment in the transverse direction in line with the movement of the target volume is carried out by a raster scanning apparatus in real time and it is consequently ensured during irradiation that the ion beam follows the moving target volume. In the concomitantly moved co-ordinate system, it again becomes necessary, in the event of movement of the tissue through which the beam passes relative to the target volume, to modify the depth of penetration of the ion beam in line with the particular tissue through which the beam is to pass.

Even though the obtainable accuracy of distribution of the administered dose will be dependent on the quality of compensation, as is shown hereinafter in FIGS. 5 and 6, it is in principle possible to achieve high degrees of homogeneity that, by virtue of the subject-matter of the present invention, are comparable with the quality of static target volumes. Precision irradiation of moving target regions, or in the case of movement of the tissue through which the beam passes, is achieved by the very accurate compensation of movement, for which purpose the raster scanning apparatus and the depth modulator correct the beam positions during irradiation at a speed that is substantially greater than the movement of the target volume or of the tissue through which the beam passes.

The corrected position is governed by the desired position in the uncorrected state and the actual displacement of the particular volume element of the target volume in the reference system of the irradiation plan. Fixed integration of movement compensation into the supervisory control system of the raster scanning apparatus makes possible a data exchange which ensures that the safety and reliability of the dose administered per unit volume of the target volume is improved despite three-dimensional movement. As a result, the subject-matter of the present invention allows the previously described raster scanning method to be extended to indications in target regions which are not capable of being fixed or not capable of being fixed adequately and/or to target regions in which the tissue through which the beam passes changes in terms of its energy-absorbing action as a result of movement. It makes it possible to irradiate tumours in the thorax and abdomen with a high degree of precision similar to that which is achievable in the case of fixed target regions.

Existing alternatives having movement correction arrangements result either in less precision or in a significantly longer duration of irradiation. Those methods can disadvantageously reduce the prospects for successful therapy or the number of patients treated per unit time. Neither of those results occurs in the case of the described subject-matter of the invention. The apparatus according to the invention can, moreover, facilitate patient positioning because, in the event of slight errors in positioning, the beam position is automatically modified. In the case of the apparatus according to the invention, strict patient fixing is no longer imperative, as a result of which patient comfort is substantially increased.

In a preferred embodiment of the invention, the raster scanning apparatus comprises two raster scanning magnets, which deflect an ion beam orthogonally in relation to a coupling-in direction into the raster scanning magnets, in an X and a Y direction, which are in turn perpendicular to one another, for scanning the area of the target volume slice-wise, the raster scanning magnets being controlled by fast-reacting power supply units. This has the advantage that transverse compensation of the transverse change in the target volume and its covering tissue due to movement can be carried out from irradiation position to irradiation position in fractions of milliseconds.

The apparatus preferably comprises at least one accelerator, by means of which the energy of the ion beam can be adjusted so that the target volume can be irradiated slice-wise, staggered in terms of depth of penetration. With this there is associated the advantage that the entire target volume can be successively scanned slice-wise, the range of the ion beam being adjustable from slice to slice by changing the energy of the ion beam. For that purpose, the accelerator substantially consists of a linear accelerator and/or a synchrotron or cyclotron, in which protons and/or heavy ions of identical mass can be adjusted step-wise in terms of their energy.

Because of the complexity of the control functions for the accelerator, modifying the energy of the ion beam to prespecified ranges within the irradiation space, especially within the target volume, is not possible with the required degree of precision in such a short time that the movements of a target volume or patient can be automatically followed. Rather, the cycles of the particle accelerator are matched to slice-wise scanning of the target volume.

Therefore, in a further preferred embodiment of the invention, the depth modulator comprises two ion-braking plates of wedge-shaped cross-section which cover the entire irradiation zone of the ion beam and allow more rapid depth scanning modification in the case of a moving target volume than increasing the ion beam energy from energy level to energy level, so that compensation of the depth of penetration from irradiation point to irradiation point becomes possible by means of a depth modulator of such a kind. For the purpose, the wedge-shaped ion-braking plates of the depth modulator are preferably arranged on electromagnetically actuatable carriages.

By means of those electromagnetically actuatable carriages, the position of the wedge-shaped ion-braking plates can be modified within fractions of milliseconds and accordingly the length of the braking path of the ions that is present in a region of overlap of the wedge-shaped braking plates can be varied by means of the ion-braking plates. For the purpose, the ion-braking plates overlap in the irradiation region of the ion beam and can accordingly modify the ions in terms of their range in line with spatial and temporal changes in the moving target volume.

The ion-braking plates are preferably mounted on linear motors. Linear motors of such a kind have the advantage that continuous fine regulation of ion braking is possible for the purpose of modifying the scanning of the target volume in terms of depth. Furthermore, shifting the position of the wedge-shaped ion-braking plates with the aid of linear motors is not only extremely precise spatially but is also capable of matching a temporal displacement of the target volume in terms of depth at an extremely fast reaction speed so that continuous tracking and compensation of movements by means of depth compensation is possible.

Alternatively, the modification of energy can also be effected by means of an electro-magnetic acceleration path in the accelerator or in the high-energy beam supply.

In a further preferred embodiment of the invention, the position location and tracking system comprises at least two measurement sensors which detect the location, in terms of time and space, of markings on a target volume-containing region of the body of a patient from two spatial angles relative to an ion beam axis. Such markings can be applied using luminous inks that are tolerable to the skin, in the form of dots, lines or other geometric shapes, or in the form of luminous elements so that they are clearly registered and measured by the measurement sensors.

In a further preferred embodiment of the invention, the measurement sensors are at least one precision video camera and/or X-ray detection means and/or ultrasound detection means, which co-operate with an image evaluation unit in the movement measurement, control and read-out module SAMB. This advantageously makes it possible for the movements of a region of the body in the vicinity of a target volume to be exactly measured and to be correlated with the temporal and spatial displacements in the location of the target volume and covering tissue, for example in the form of a stored look-up table.

Irradiation of a tumour volume is in principle composed of image points set out in relation to one another in raster form in a planar arrangement in slice form, the ion beam being deflected by means of the raster scanning apparatus from irradiation point to irradiation point orthogonally to its beam axis in an X direction and a Y direction; the apparatus comprising, for the purpose of location detection, a multiwire proportional chamber as a location-sensitive detector, which is arranged in the beam direction upstream of the depth modulator and which forwards actual positions of the ion beam to a location measurement, control and read-out module for compensation of discrepancies between the actual transverse position and the desired transverse position based on an irradiation plan and on actual deviation of the target volume due to movement.

Even if the energy of the ions in an ion beam can be kept constant by the accelerator in question, the number of ions per unit volume over time is still not constant. In order nevertheless to maintain an ion beam dose of equal magnitude at each volume point of the tumour tissue and accordingly to provide dose homogeneity, an ionisation chamber having a fast read-out is, in a preferred embodiment of the invention, arranged as a transmission counter in the beam path of the ion beam for the purpose of monitoring the intensity of the ion beam stream. A transmission counter of such a kind determines the dwell time of the ion beam at a volume point of the target volume to be irradiated, and a control and read-out module, SAMI, associated therewith delivers a signal to the read-out module to address the next volume point as soon as a pre-specified beam dose has been reached. Accordingly, it is advantageously possible for a volume slice of the tumour volume over a planar extent to be scanned raster-wise from irradiation point to irradiation point. Preferably, the ionisation chamber is arranged between the deflecting device and the depth modulator, especially as the depth modulator, with its wedge-shaped ion-braking plates, controls ions solely in terms of their range without influencing the ion dose.

A method for compensation of three-dimensional movements of a target volume on a patient couch during ion beam irradiation using a raster scanning apparatus comprises the following method steps. First, a healthy tissue structure covering the target volume in the upstream direction of the beam is detected in preliminary investigations and a digital model of the detected structure of the covering healthy tissue is produced. That model is stored in a memory of the movement control and read-out module SAMB, for example in the form of a look-up table. The target volume can then be positioned on a patient couch.

During irradiation, three-dimensional movements of the target volume are detected in real time by means of a position location and tracking system. The movements are then divided vectorially into longitudinal and transverse components, and the transverse components of the movements are compensated by corrective control of raster scanning magnets of the raster scanning apparatus. The longitudinal components of the movements are finally compensated by comparison with the data of the stored model and comparison-based modification of the settings of a depth modulator.

Accordingly, the invention advantageously makes available a method for three-dimensional compensation of target region movements in real time during ion irradiation, for example with protons or heavy ions. For the purpose, transverse excursion of the beam by the raster scanning system is combined with additional depth modulation. From the current measured deviation in the location and position of the particular volume element of the target volume from the reference position used in planning, especially taking into account the particular tissue through which the beam passes, a dynamic correction vector is determined and broken down into transverse and longitudinal components. The longitudinal component takes the particular tissue through which the beam passes into account in the calculation and determines the energy required to bring about the interaction of the ions in the particular volume element in the target volume.

The transverse components are added as a dynamic offset to the desired position of the raster scanning system and the longitudinal component governs the setting of the depth modulator. By that means, the beam position is re-adjusted dynamically in all three spatial directions in line with the three-dimensional target region movement. As a result of complete integration into the supervisory irradiation control system of the ion beam therapy facility by means of a movement measurement, control and read-out module SAMB, the temporal sequence of irradiation is usually not affected. Direct communication between the individual electronics modules of the supervisory control system makes possible the availability of consistent, dynamic movement data in the entire system.

For the purpose, preferably, in the preliminaries to irradiation, a digital model of the structure of tissue covering the target volume in the upstream direction of the beam is detected by means of X-ray and/or ultrasound investigations. Using such investigations in the preliminaries to irradiation, modifying the dose escalation in terms of depth during ion irradiation, in the case of movement, can be compensated very precisely in real time with re-adjustment of the depth modulator by means of the fact that longitudinal depth correction is carried out by means of the depth modulator from beam position to beam position.

In a preferred example of carrying out the method, location measurement is registered and evaluated using a multiwire proportional chamber by way of a location measurement, control and read-out module SAMO. For the purpose of transverse compensation, information which is stored in the location measurement, control and read-out module SAMO of a supervisory control system and relates to the desired position of an irradiation plan is compared with the measured actual position of the beam position from the location-sensitive detector in real time taking into account the detected transverse movement component of the target volume, and transverse location compensation in the X and Y direction is carried out by means of the fast scanner magnet power supply units in co-operation with a control and read-out module SAMS for the raster scanning magnets of the raster scanning apparatus.

In a preferred example of carrying out the method, a controlled, short-duration interruption in the event of the occurrence of unforeseen movement conditions outside the working range of compensation ensures flexible and yet safe use for any kind of movement. For that purpose, fast shut-down of the beam is initiated by the location measurement, control and read-out module SAMO of the location-sensitive detector in real time and/or by the movement, control and read-out module SAMB of the depth modulator, if the difference between a measured value and a desired value of the transverse beam position and/or of the longitudinal depth of penetration, respectively, exceeds a threshold value that can be set in the real-time software of the control and read-out modules SAMO and/or SAMB.

In addition, besides correcting the desired position of the ion beam and controlling the depth modulator, the SAMB is responsible for monitoring faults in, or the failure of, the connected sub-systems for a position location and location tracking method and for depth modulation. The SAMB checks the resulting values for consistency and coherency and in the event of a fault initiates a corresponding interlock signal which interrupts irradiation. If the requisite correction parameters exceed the limits fixed in the course of preliminaries, the irradiation is interrupted for a short time until the values are again within the allowed range.

The invention will now be explained in greater detail with reference to the accompanying FIGS. 3-6.

Figure 3:
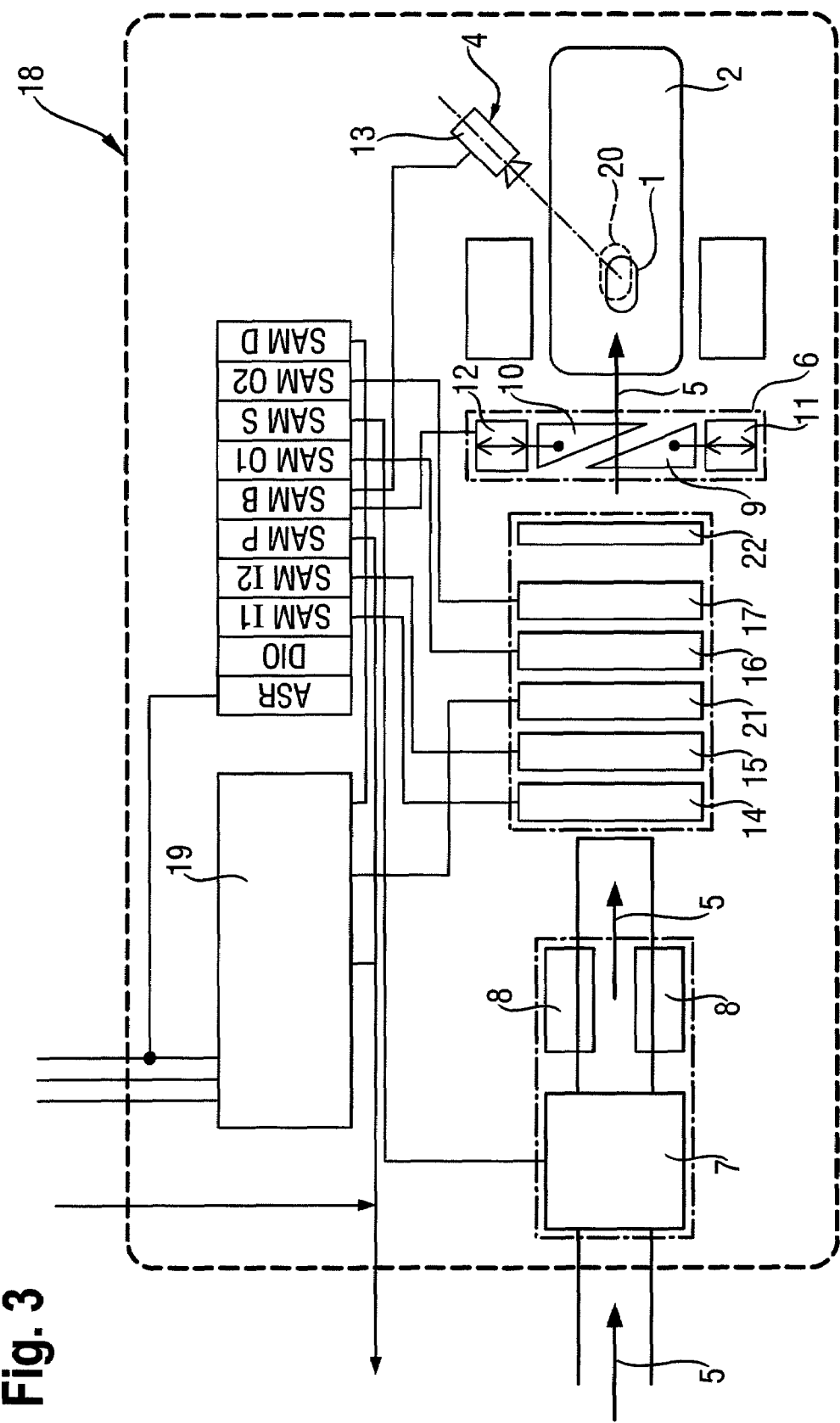
FIG. 3 is a generalised representation of an arrangement and connection schema of the components of an apparatus according to an embodiment of the invention.

FIG. 3 is a generalised representation of an arrangement and connection schema of the components of an apparatus according to a first embodiment of the invention. For the purpose, reference numeral 1 denotes a target volume and the broken line 20 denotes a three-dimensional movement of the target volume 1 on a patient couch 2. Reference numeral 3 denotes a raster scanning apparatus, which comprises a raster scanning magnet 7 for X excursion of an ion beam 5 consisting of protons or heavy ions and which comprises a further raster scanning magnet 8 for Y deflection of the ion beam 5.

After the raster scanning apparatus 3, the ion beam 5 passes through a plurality of measurement chambers 23, of which ionisation chambers 14 and 15 serve to detect the dose of the ion beam 5, and multiwire proportional chambers 16 and 17 serve to measure the spatial positions of the ion beam 5 and, for the purpose, are arranged in the ion beam 5 in the beam direction upstream of a depth modulator 6. In addition, the ion beam 5 passes through an additional measurement chamber 21 for limit value monitoring, which is in direct operative connection with a supervisory control computer 19 of the irradiation room 18. In addition, the ion beam 5 also passes through a comb filter 22 before the depth modulator 6.

The depth modulator 6 is arranged in front of the target volume 1 and comprises two wedge-shaped ion-braking plates 9 and 10, which, for depth modulation, can be moved relative to one another by means of linear motors 11 and 12 in order to carry out depth of penetration compensation taking into account the changes in the healthy tissue and the change in location of the target volume 1 in the event of movements of the patient on the patient couch 2.

For the detection of movement, the irradiation room 18 has a position location and tracking system 4 which has, as measurement sensor, at least one precision video camera 13 and/or X-ray detection means and/or ultrasound detection means which is in operative connection with a control and read-out module SAMB for movement compensation.

FIG. 3 accordingly shows an embodiment of an irradiation system according to the invention for an intensity-, location- and movement-modulated raster scanning method. The hardware overview of FIG. 3 constitutes a further development of the system of the subject-matter described in DE 100 31 074 A1 and EP 99 107 121, by means of which the precision irradiation of moving target regions is improved. The improvement in this irradiation system is achieved by the bringing together of the raster scanning system and the depth modulator and also by the processing of movement information measured in real time by the addition of a further electronics module SAMB to the supervisory control system and by using further communications interfaces and improved digital models.

The invention accordingly makes possible improved dynamic three-dimensional re-adjustment of the therapy beam in real time with fine resolution and extremely high accuracy.

Figure 4:
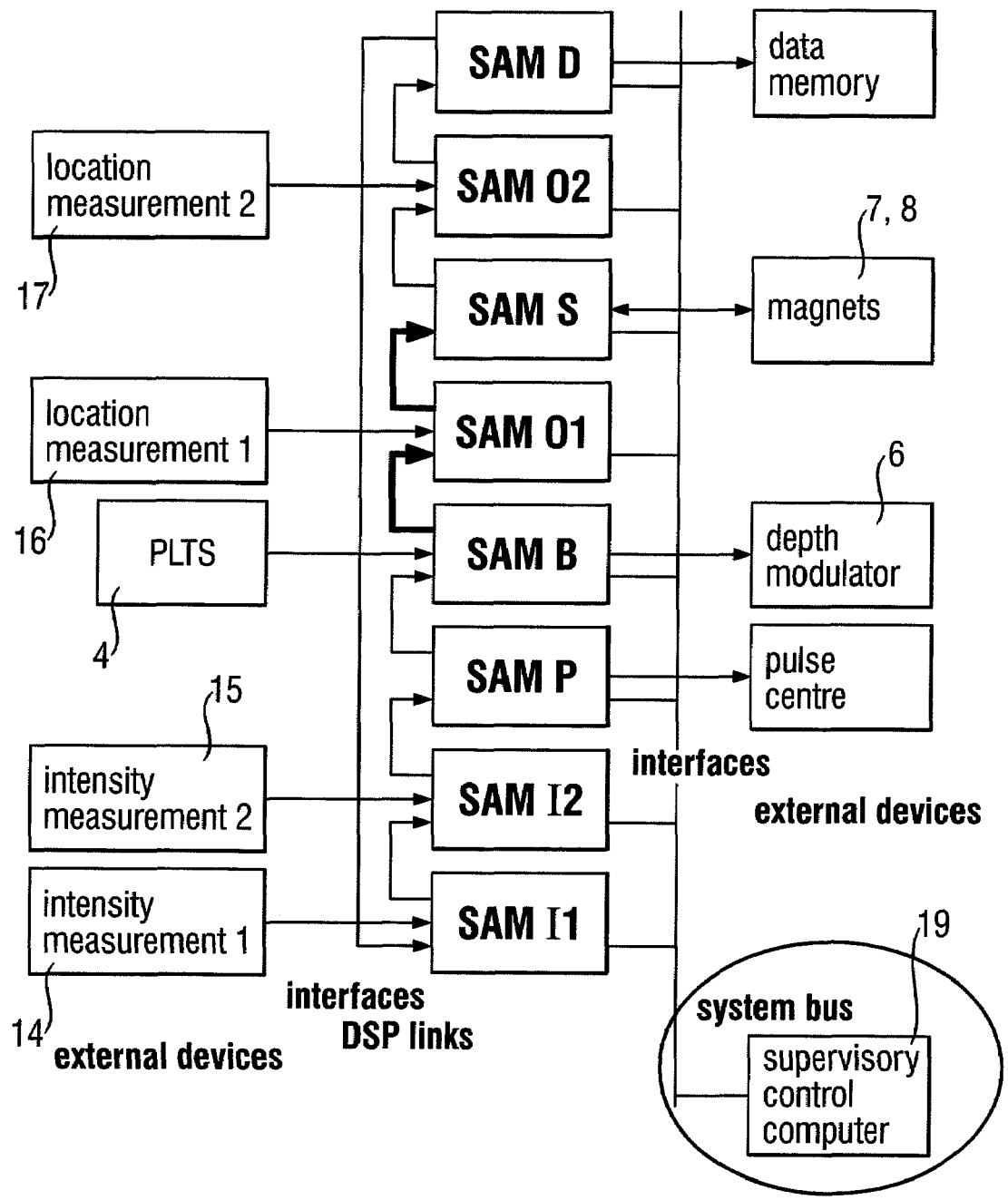
FIG. 4 shows, in diagrammatic form, a block circuit diagram of the control and read-out modules, together with connected external devices, of an apparatus according to FIG. 3.

FIG. 4 shows, in diagrammatic form, a block circuit diagram of the control and read-out modules SAM, together with connected external devices, of an apparatus according to FIG. 3. By means of FIG. 4 it is shown that the apparatus according to the invention and the method according to the invention are fully integrated into a supervisory irradiation control system, which is composed of a system control and sequence control and a supervisory control computer 19. In this exemplifying embodiment, the sequence control of the supervisory control system consists of a plurality of electronics modules, the control and read-out modules SAM having various functions, and the sequence control computer ASR.

There is also a dedicated module SAMB exclusively for the compensation of target region movements. For safety-related reasons, a second, identical module can be used, which allows consistency checks on the data stream. The SAMB module is located in the data chain, which is shown in FIG. 4 by arrows, for example upstream of location measurement SAMO 1. The real time software on the SAMB reads movement information, at a fixed time interval, from the position and location tracking system 4 connected by way of an interface and, with the aid of a look-up table calculated in the course of preliminaries, determines the requisite compensation vector in the reference system of irradiation treatment.

The frequency of movement measurement can be freely adapted to the particular position location and location tracking method and to the requisite measurement accuracy, for example 10 Hz to 100 Hz. If the length of the measurement interval exceeds the duration of location measurement in the supervisory control system, the determined compensation vector remains current until the next cycle of movement registration with the aid of the position location and location tracking system 4.

In each measurement cycle of rapid location correction, for example in 150 µs, the SAMB ascertains the current transverse beam position from the stored desired data set and provides it with the transverse components of the current compensation vector. That new desired position is forwarded by way of an interface in the real time control by way of SAMO 1 to the control SAMS of the raster scanning magnets 7 and 8, which compares that value with the current measured actual position of SAMO 1 and, where appropriate, corrects the transverse beam position by way of a feedback control loop.

The modified desired position and movement information are forwarded to all other modules of the supervisory control system for the purposes of logging and data consistency. Furthermore, from the desired longitudinal beam position and the determined longitudinal compensation component, SAMB calculates the settings of the depth modulator 6. Controlling the depth modulator 6 is carried out directly by way of an interface of the SAMB. FIG. 4 accordingly shows, by way of example, the data flow and the requisite interfaces.

Figure 1:
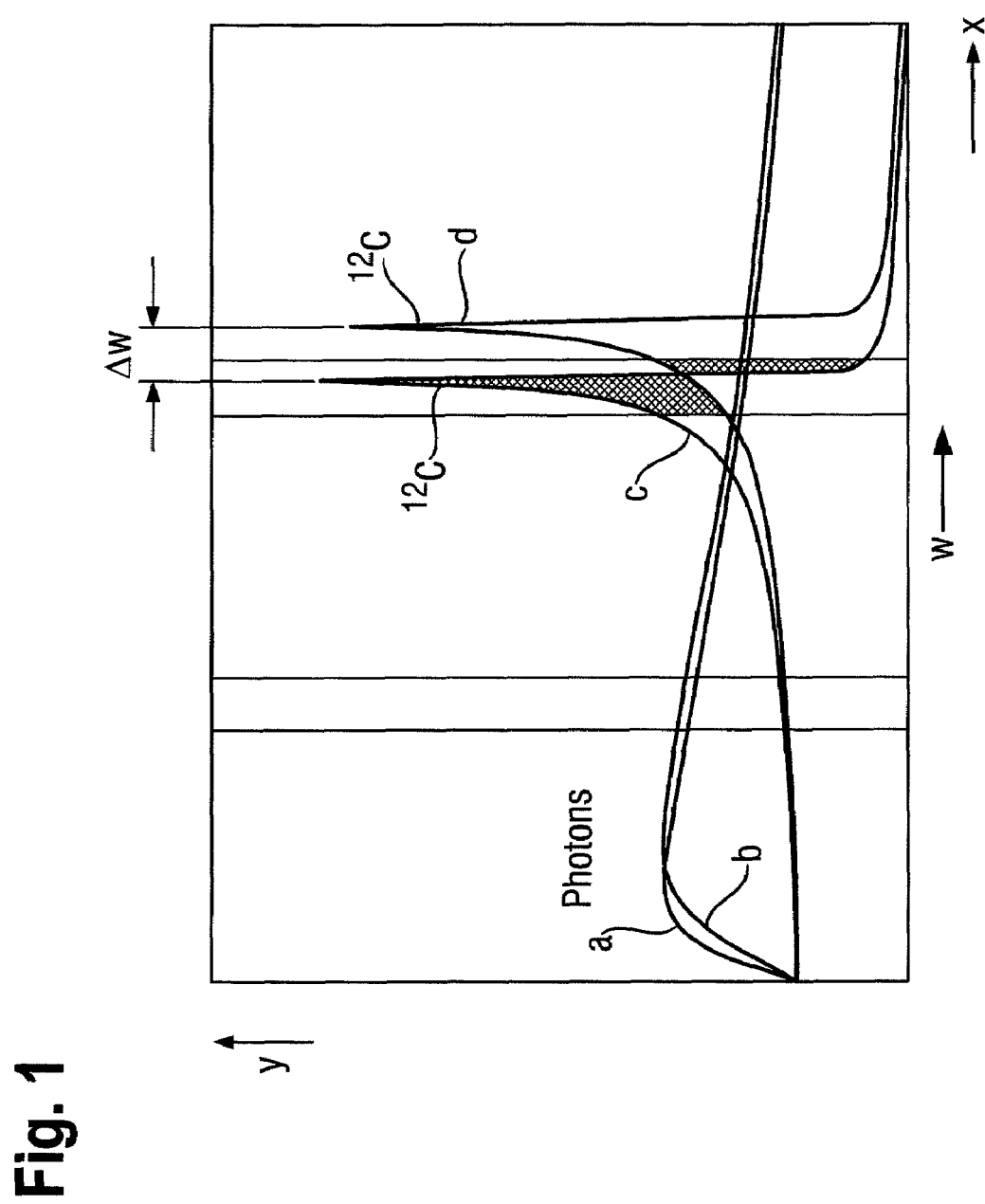
Figure 2:
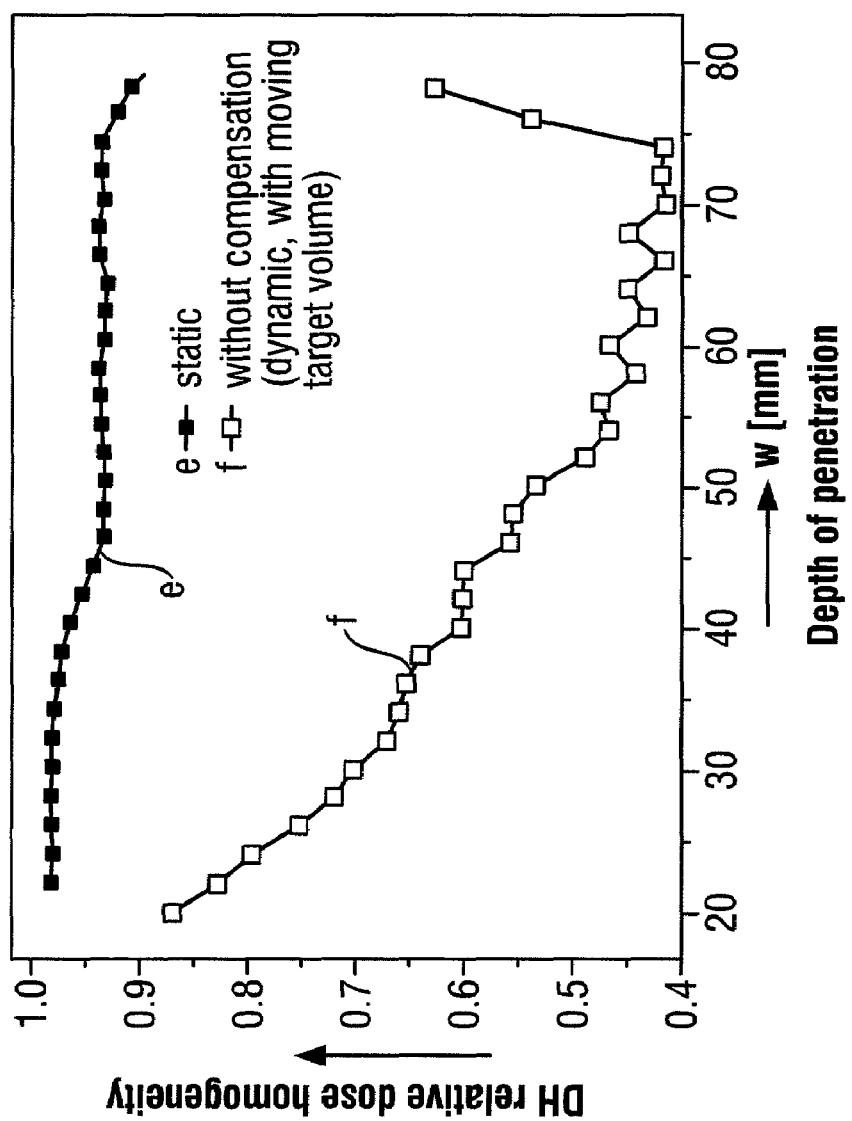
Figure 5:
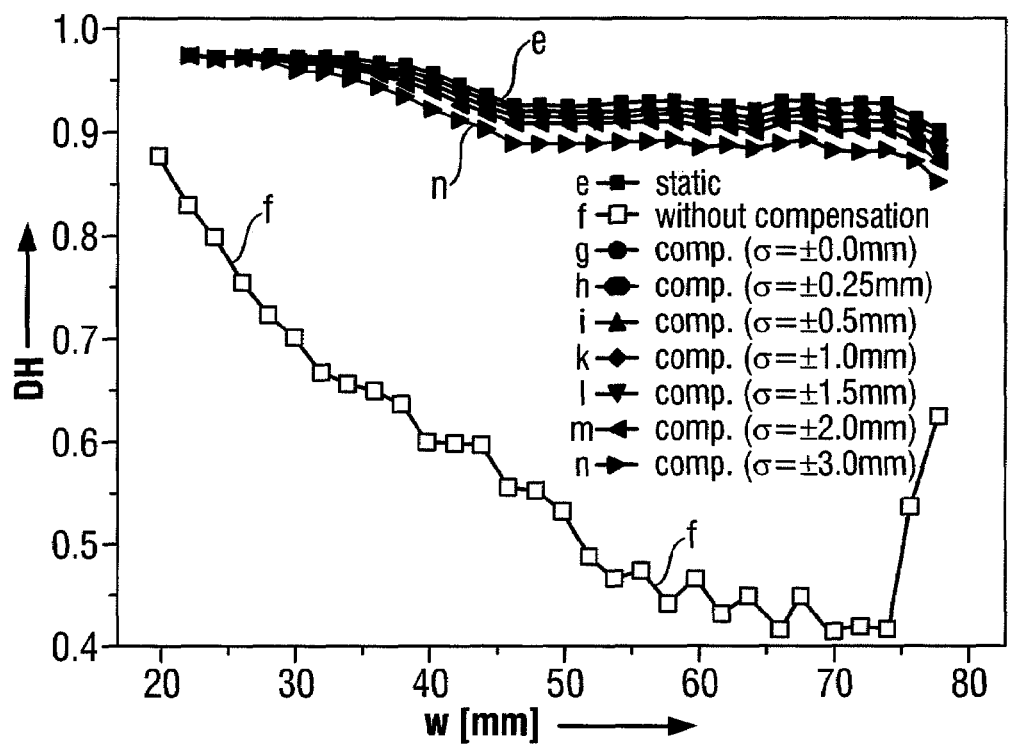
FIG. 5 shows, in diagrammatic form, results of movement compensation with respect to relative dose homogeneity in dependence upon depth of penetration when the movement can be detected with different degrees of variance from 0.0 mm to 3.0 mm.

FIG. 5 shows, in diagrammatic form, by curves g to n, results of movement compensation with respect to relative dose homogeneity, DH, in dependence upon depth of penetration, w in mm, when movement compensation can be carried out with differing degrees of variance from $\sigma=\pm0.0$ mm (curve g) to $\sigma=\pm3.0$ mm (curve n). As a result of compensation using the apparatus according to the invention and the method according to the invention, a dose homogeneity is accordingly achieved which, despite a moving target volume, approximately reaches the dose homogeneity in the case of a target volume which is static, that is to say fixed on the patient couch. By way of comparison, these results are set against the relative dose homogeneity without compensation measures as shown in curve f and as also shown in FIG. 2.

Figure 6:
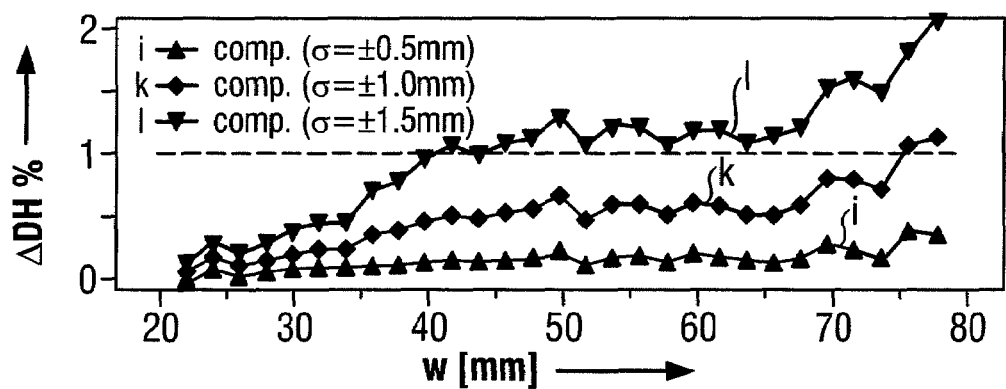
FIG. 6 shows, in diagrammatic form, results of movement compensation, to an enlarged scale, with respect to percentage deviation of relative dose homogeneity in dependence upon depth of penetration in the case of a static target volume when the movement can be detected with a variance of 0.5 mm, 1.0 or 1.5 mm.

FIG. 6 shows, in diagrammatic form, results of movement compensation, to an enlarged scale, with respect to percentage deviation, $\Delta DH$, of dose homogeneity in percent of dose homogeneity, DH, of a static target volume, in dependence upon depth of penetration, w in mm, when the movements can be detected and compensated with a variance of $\sigma=\pm0.5$ mm (curve i), $\sigma=1.0$ mm (curve k) and $\sigma=1.5$ mm (curve l).

Figure 7:
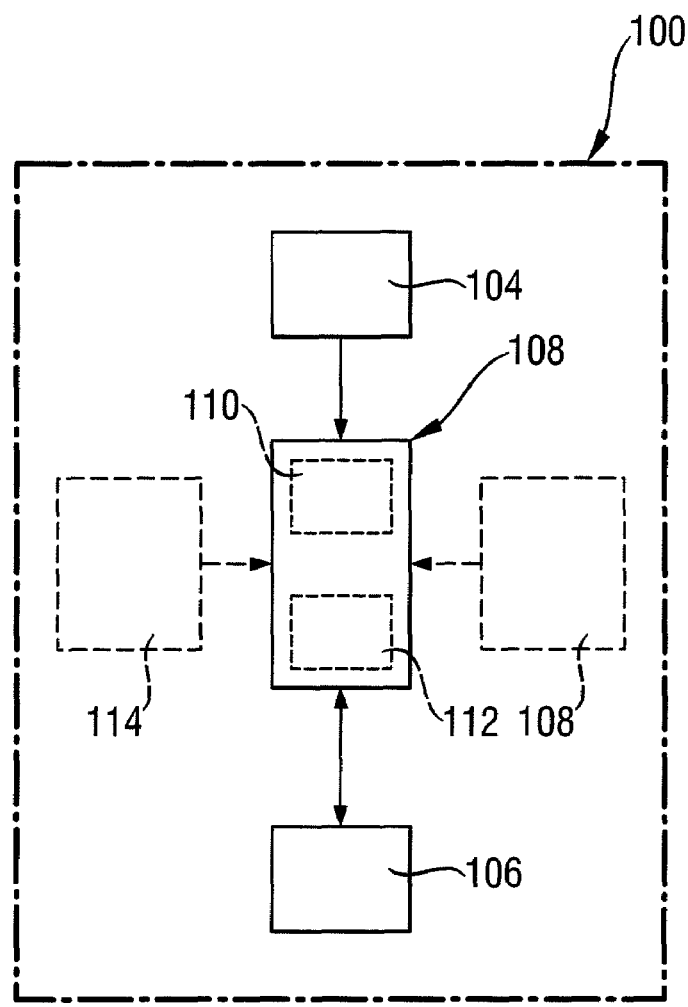
FIG. 7 shows, in diagrammatic form, a block diagram of an apparatus according to an embodiment of the invention.

FIG. 7 illustrates the invention by way of the example of an apparatus 100 for modifying the depth of penetration W, shown in FIGS. 1, 8, 9 and 10, of an ion beam, in dependence upon a patient's movement, that is to say in dependence upon movement of regions of the body of the patient, for example the breathing movement of the chest. The apparatus 100 comprises a position location and tracking system 104 for monitoring movements of the patient, a depth modulator 106 for adjusting the depth of penetration of the ion beam into the patient and a movement measurement and control unit 108, which is in operative connection with the position location and tracking system 104 and the depth modulator 106.

The movement measurement and control unit 108 comprises a microprocessor 110 having a memory, in which data of a model 112 have been stored. The model 112 describes the structure of healthy tissue which covers the target volume in the upstream direction of the beam and accordingly through which the ion beam must pass on irradiation. A model of such a kind is known, for example, from "A. Schweikard et al: Robotic motion compensation for respiratory movement during radiosurgery. Comput Aided Surg. 2000;5(4):263-77".

The movement measurement and control unit 108 receives information relating to the movement of the patient from the position location and tracking system 104. The unit, with the aid of the microprocessor, processes that information together with the model, in order to make available a control signal for the depth modulator 106. That control signal should control the depth modulator 106 in such a manner that the depth of penetration of the ion beam is always adjusted, irrespective of the movement of the patient, to the target volume element to be irradiated at the particular moment in the target volume (tumour) in the patient. (Hereinafter "target volume" and "target volume element" are sometimes used synonymously because the more precise meaning will emerge from the particular context.) For the purpose, especially the movement of the healthy tissue relative to the target volume element is required because different energy absorptions of the particle beam take place in the patient in dependence upon the healthy tissue that the beam passes through and accordingly the depth of penetration of the ion beam changes in dependence upon the tissue that the beam passes through in the event of movement of the healthy tissue relative to the target volume element. The change in range of the ion beam in dependence upon the tissue that the beam passes through can be calculated, for example, on-line during irradiation or determined with the aid of tables produced, for example, during therapy planning, which represent various tissue arrangements.

In an expanded embodiment of the apparatus 100 for modifying the depth of penetration, additional means 114 for obtaining location information relating to the location of the ion beam relative to the patient may be provided. That location information can in turn be used together with the aid of the model and the information relating to the movement of the patient for the purpose of controlling a raster scanning apparatus 116. As a result, the ion beam can follow a movement of the target volume in a transverse direction to the ion beam, it simultaneously being possible, in dependence upon the movement of the healthy tissue relative to the target volume, for the depth of penetration to be modified.

Figure 8:
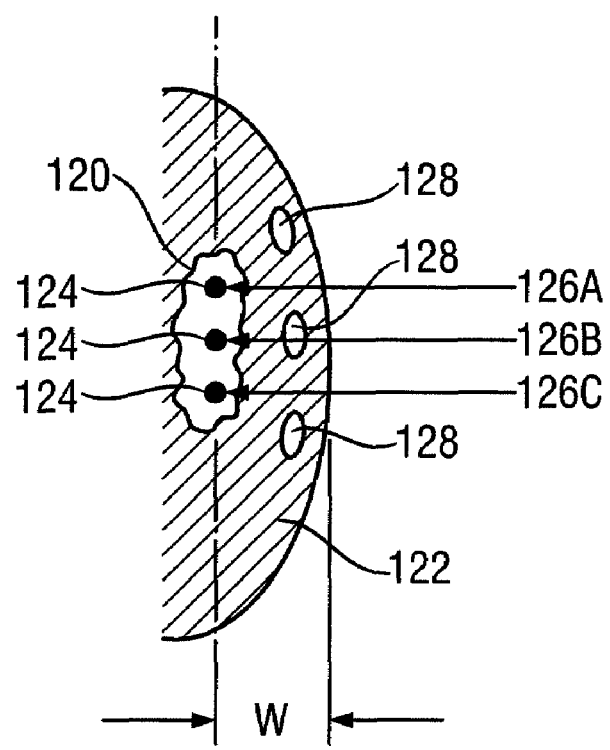
FIG. 8 shows, in diagrammatic form, a static case of irradiation of a target volume.

FIG. 8 shows an aspect, relevant to the invention, during beam therapy in a static situation, wherein neither the target volume 120, or tumour tissue 120, nor the covering tissue 122, or healthy tissue 122, through which the beam passes during therapy, move. Three irradiation points 124 (target volume elements) are shown in diagrammatic manner, which are in each case irradiated by the ion beams 126A, 126B and 126C. During therapy planning, the tissue 122 through which the beam passes is analysed. In order to reach the beam position 124 at a depth W, the ion beam energy is modified in line with the covering volume 122 through which the beam passes. In the process it is taken into account whether the beam passes through, for example, bone 128, as is the case for the ion beam 126B, or whether it does not (ion beams 126A and 126C).

Figure 9A:
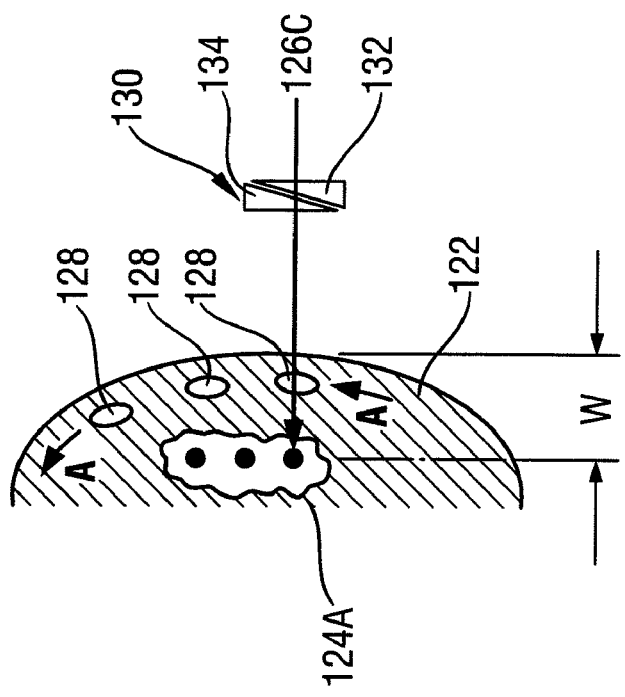
FIG. 9 shows, in diagrammatic form, a dynamic case of irradiation of a static target volume having a moving covering volume.
Figure 9B:
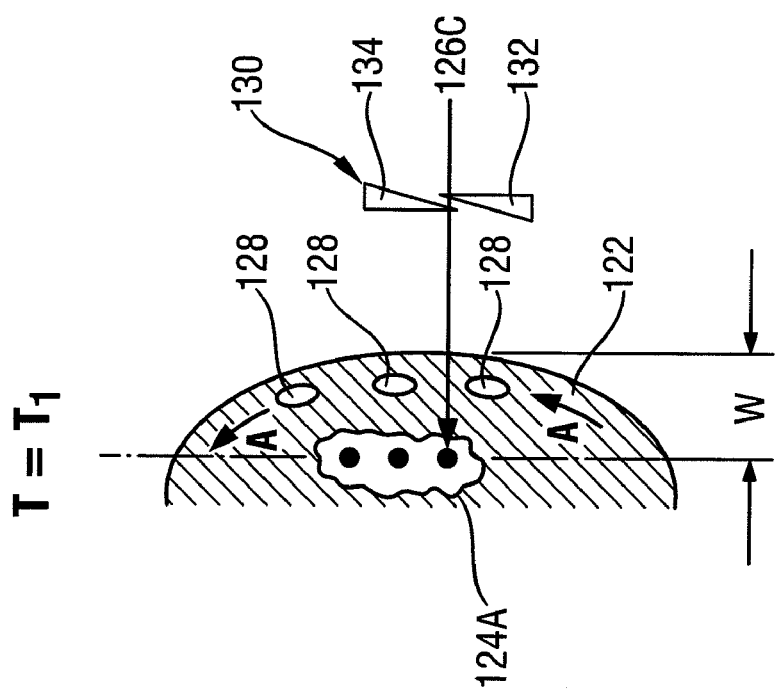

FIG. 9 then supplements the schema of FIG. 8 with patient movement; in this case, by way of example, the bones 128 correspond to the ribs of the chest and, during breathing, they move in the direction of the arrows A relative to the static target volume 120. In the case of non-moving tumour tissue 124A, for beam position 126C the composition of the particular covering volume 122 through which the beam passes changes in the course of breathing and in the course of irradiation: at timepoint T=T1 the beam does not pass through a rib 128 and at timepoint T=T2 the beam does pass through a rib 128. Accordingly, the beam energy must be modified in time-dependent manner in order to ensure that the ion beam 126C has the depth of penetration W on irradiation. For that purpose, the position location and tracking system monitors movements of the patient, in this case the movements of the chest, and transmits that information to the movement measurement and control unit, in which the model of the covering volume 122 through which the beam passes is compared and appropriate depth modulation of a depth modulator 130 is brought about. For example, the wedges 132 and 134 of the depth modulator 130 overlap to a greater extent at timepoint T2 than at timepoint T1.

Figure 10A:
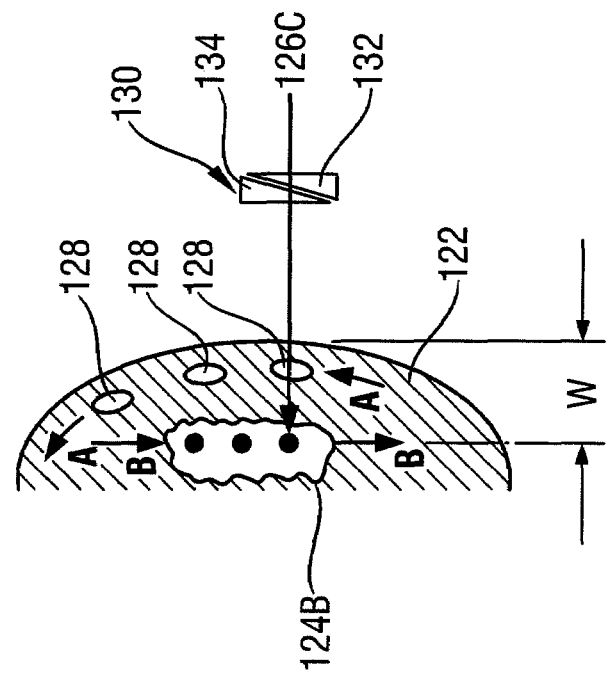
FIG. 10 shows, in diagrammatic form, a dynamic case of irradiation of a moving target volume and a moving covering volume.
Figure 10B:
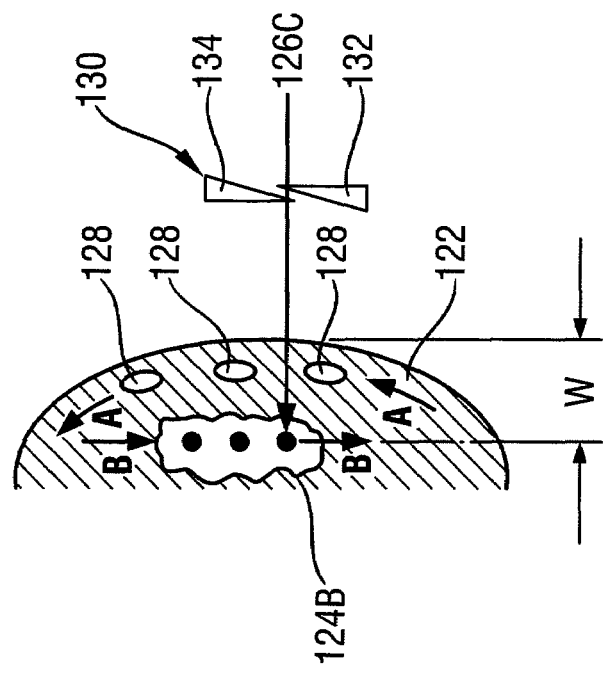

FIG. 10 then additionally takes into account the movement of the target volume 124B itself in direction B. Monitoring movements of the patient also allows, by means of the model, determination of the movement of the target volume. For example, in FIG. 10b, at timepoint T2, the tumour tissue 124B has moved downwards in the direction of arrows B and the healthy tissue 122 has moved upwards in the direction of arrows A. It is the function of a beam re-adjustment apparatus, for example of a raster scanning apparatus, to move the ion beam 126C, for example parallel to 126C, in a downwards direction so that the irradiation point 124 in question is always irradiated. In accordance with the invention it is now also possible, with the aid of the model, to take into account the changed conditions due to the relative movement of tumour tissue 124B and healthy tissue 122 when the beam passes through the healthy tissue 122 and in turn to control the depth modulator accordingly.

The possibilities for carrying out correction of the depth of penetration in accordance with the invention are not limited to the known raster scanning method in the case of particle therapy as outlined at the beginning but can also be used in the case of intensity-modulated irradiation. In the process, in contrast to the raster scanning method, small regions of area are masked out, for example using multi-leaf collimators, and set against one another at varying intensities.

LIST OF REFERENCE SYMBOLS 1 target volume
2 patient couch
3 raster scanning apparatus
4 position location and tracking system
5 ion beam
6 depth modulator
7 raster scanning magnet (X deflection)
8 raster scanning magnet (Y deflection)
9 wedge-shaped ion-braking plate
10 wedge-shaped ion-braking plate
11 linear motor
12 linear motor
13 precision video camera; X-ray detection means; ultrasound detection means
14 ionisation chamber
15 ionisation chamber
16 multiwire proportional chamber
17 multiwire proportional chamber
18 treatment room
19 supervisory control computer
20 broken line
21 additional measurement chamber
22 comb filter
23 measurement chambers
100 apparatus for modifying the depth of penetration
104 position location and tracking system
106 depth modulator
108 movement and control unit
110 microprocessor
112 model
120 target volume or tumour tissue
122 covering volume or healthy tissue through which the beam passes
124 irradiation point
124A beam position
126A ion beam 126B ion beam
126C ion beam
128 bone
130 depth modulator
132 wedge
134 wedge
A direction of arrows
B direction of arrows
T time
$T_1$ timepoint
$T_2$ timepoint difference between measurement value and desired value
Δw change in depth of penetration
w depth of penetration
SAMO1 location measurement, control and read-out module
SAMO2 location measurement, control and read-out module
SAMS control and read-out module of the raster scanning magnets
SAMB movement measurement, control and read-out module

The invention claimed is:

1. Apparatus for compensation of three-dimensional movements of a target volume (1) on a patient support apparatus (2) during ion beam irradiation using a raster scanning apparatus (3), wherein a compensation apparatus comprises:

a position location and tracking system (4) which detects the three-dimensional movements of the target volume (1), and a depth modulator (6) which re-adjusts the depth of penetration w of the ion beam (5), the raster scanning apparatus (3), which deflects the ion beam (5) transversely and which is in operative connection with a location measurement, control and read-out module (SAMO) and a module for changing the beam excursion (SAMS), wherein the position location and tracking system (4) is in operative connection with a movement measurement, control and read-out module SAMB;

and the depth modulator (6) is in operative connection with the movement measurement, control and read-out module SAMB, and the movement measurement, control and read-out module (SAM B) comprising a microprocessor having a memory, and the memory comprising data of a model of a structure of healthy tissue that covers the target volume (1) in the upstream direction of the beam, and the microprocessor comprising computational components which break down the detected movements of the target volume (1) vectorially into longitudinal and transverse components relative to the ion beam (5) and which compare the longitudinal components with the stored model for correction of the depth of penetration w of the ion beam (5).

2. Apparatus according to claim 1, wherein the raster scanning apparatus (3) comprises two raster scanning magnets (7, 8), which deflect an ion beam (5) orthogonally in relation to a coupling-in direction into the raster scanning magnets (7, 8), in two directions preferably arranged orthogonally relative to one another, which are in turn arranged perpendicular to one another, for scanning the area of the target volume (1) slice-wise.

3. Apparatus according to claim 2, wherein the raster scanning magnets (7, 8) are controlled by fast-reacting power supply units.

4. Apparatus according to claim 1, wherein the apparatus comprises ion acceleration elements by means of which the energy of the ion beam (5) can be adjusted so that the target volume (1) can be irradiated slice-wise, staggered in terms of depth of penetration w.

5. Apparatus according to claim 1, wherein the depth modulator (6) comprises two ion-braking plates (9, 10) of wedge-shaped cross-section which cover the entire irradiation zone of the scanned ion beam (5).

6. Apparatus according to claim 5, wherein the ion-braking plates (9, 10) are mounted on linear motors (11, 12).

7. Apparatus according to claim 5, wherein the ion-braking plates (9, 10) are arranged on electromagnetically actuatable carriages.

8. Apparatus according to claim 5, wherein the ion-braking plates (9, 10) are displaceable relative to one another with their wedge-shaped crosssections overlapping in the region of the ion beam (5).

9. Apparatus according to claim 1, wherein the position location and tracking system (4) has at least one precision video camera (13) and/or X-ray detection means and/or ultrasound detection means, which are in operative connection with an image evaluation unit in the movement measurement, control and read-out module SAMB.

10. Apparatus according to claim 1, wherein an ionisation chamber (14, 15) having a fast read-out for monitoring the intensity of the ion beam stream is arranged as a transmission counter in the beam path of the ion beam (5).

11. Apparatus according to claim 1, wherein the ionisation chamber (14, 15) is arranged between the raster scanning apparatus (3) and the depth modulator (6).

12. Apparatus according to claim 11, wherein a multiwire proportional chamber (16, 17) is arranged as a location-sensitive detector in the beam direction upstream of the depth modulator (6).

13. Apparatus for modifying the depth of penetration of an ion beam in dependence upon movement of a patient on a patient support apparatus of a therapy facility, comprising a position location and tracking system (4) for monitoring movements of the patient, a depth modulator for adjusting the depth of penetration of the ion beam into the patient, and a movement measurement and control unit which is connected to the position location and tracking system (4) and to the depth modulator and which receives information relating to the movement of the patient from the position location and tracking system (4) and controls the depth modulator for modifying the depth of penetration, wherein the movement measurement and control unit comprises a microprocessor having a memory, and the memory comprising data of a model of a structure of healthy tissue that covers the target volume in the upstream direction of the beam, and the microprocessor, with the aid of the model and the information relating to the movement of the patient, so controlling the depth modulator that the depth of penetration of the ion beam is adjusted to a target volume element in the patient irrespective of the movement of the patient, especially irrespective of the movement of the healthy tissue relative to the target volume.

14. Apparatus according to claim 13, wherein the energy absorption of the tissue that the beam passes through and, as a result, the change in the range of the ion beam in dependence upon the tissue that the beam passes through can be calculated from the model.

15. Apparatus according to claim 13, wherein the tissue through which the beam is to pass can be determined from the information relating to the movement of the patient and the model.

16. Apparatus according to claim 13, wherein the model correlates changes in the electron density distribution in the healthy tissue (for example, obtained by means of multidimensional projection radiographs or from time-resolved CT data sets) with movement states of the body.

17. Apparatus according to claim 13, wherein the depth modulator for modifying the depth of penetration includes an apparatus for modifying the kinetic energy of the ions.

18. Apparatus according to claim 13, wherein the apparatus additionally comprises means of obtaining location information relating to the location of the ion beam relative to the patient, the movement measurement and control unit so controlling a raster scanning apparatus on the basis of the location information together with the aid of the model and the information relating to the movement of the patient that the ion beam follows a movement of the target volume in a transverse direction to the ion beam.

19. Apparatus according to claim 13, wherein the raster scanning apparatus (3) comprises two raster scanning magnets (7, 8), which deflect an ion beam (5) orthogonally in relation to a coupling-in direction into the raster scanning magnets (7, 8), in two directions preferably arranged orthogonally relative to one another, which are in turn arranged perpendicular to one another, for scanning the area of the target volume (1) slice-wise.

20. Apparatus according to claim 19, wherein the raster scanning magnets (7, 8) are controlled by fast-reacting power supply units.

21. Apparatus according to claim 13, wherein the apparatus comprises ion acceleration elements by means of which the energy of the ion beam (5) can be adjusted so that the target volume (1) can be irradiated slice-wise, staggered in terms of depth of penetration w.

22. Apparatus according to claim 13, wherein the depth modulator (6) comprises two ion-braking plates (9, 10) of wedge-shaped cross-section which cover the entire irradiation zone of the scanned ion beam (5).

23. Apparatus according to claim 22, wherein the ion-braking plates (9, 10) are mounted on linear motors (11, 12).

24. Apparatus according to claim 22, characterised in that the ion-braking plates (9, 10) are arranged on electromagnetically actuatable carriages.

25. Apparatus according to claim 22, wherein the ion-braking plates (9, 10) are displaceable relative to one another with their wedge-shaped cross-sections overlapping in the region of the ion beam (5).

26. Apparatus according to claim 13, wherein the position location and tracking system (4) has at least one precision video camera (13) and/or Xray detection means and/or ultrasound detection means, which are in operative connection with an image evaluation unit in the movement measurement, control and read-out module SAMB.

27. Apparatus according to claim 13, wherein a multiwire proportional chamber (16, 17) is arranged as a location-sensitive detector in the beam direction upstream of the depth modulator (6).

28. Apparatus according to claim 13, wherein the apparatus for detecting the structure of the healthy tissue covering the target volume in the upstream direction of the beam comprises X-ray and/or ultrasound detection in the preliminaries to and during ion beam irradiation.

29. Apparatus according to claim 13, wherein the raster scanning magnets (7, 8) comprise scanner magnet current power supply units for horizontal and vertical correction by means of control and read-out modules (SAMS) for the raster scanning magnets (7, 8).

30. Apparatus according to claim 13, wherein, for location measurement, a multiwire proportional chamber (16, 17) is provided by way of a location measurement, control and read-out module (SAMO), it being possible, for the purpose of transverse compensation, to compare information stored in the location measurement, control and read-out module (SAMO) of a supervisory control system relating to the desired position of an irradiation plan with the measured actual position of the beam position from the location-sensitive detector in real time taking into account the detected transverse movement component of the target volume (1).

31. Apparatus according to claim 13, wherein, for location correction in the transverse X and Y directions, the scanner magnets comprise power supply units of the raster scanning apparatus (3) comprise and longitudinal depth correction of the depth modulator (6) from beam position to beam position is provided.

32. Apparatus according to claim 13, wherein fast shutdown of the beam by the location measurement, control and read-out module (SAMO) of the location-sensitive detector in real time and/or by the movement measurement, control and read-out module (SAMB) of the depth modulator (6) is possible, if the difference between a measured value and a desired value of the transverse beam position and/or of the longitudinal depth of penetration w exceeds a threshold that can be set in the realtime software of the control and read-out modules SAMO and/or SAMB.

33. Method for compensation of three-dimensional movements of a target volume (1) on a patient couch (2) during ion beam irradiation using a raster scanning apparatus (3), the method comprising the following method steps:

detecting a structure of healthy tissue covering the target volume (1) in the upstream direction of the beam;

producing a digital model of the detected structure of the covering healthy tissue;

storage of the model in a memory of the movement measurement, control and readout module (SAMB);

positioning of the target volume (1) on a patient couch (2) in a treatment room (18);

detecting three-dimensional movements of the target volume (1) in real time during the irradiation procedure by means of a position location and tracking system (4);

vectorially dividing the movements into longitudinal and transverse components;

compensating the transverse components of the movements by corrective control of raster scanning magnets (7, 8) of the raster scanning apparatus (3);

compensating the longitudinal components of the movements by comparison with data of the stored model and comparison-based modification of the settings of a depth modulator (6).

34. Method according to claim 33, wherein detecting the structure of the healthy tissue covering the target volume in the upstream direction of the beam is carried out by means of X-ray and/or ultrasound detection in the preliminaries to and during ion beam irradiation.

35. Method according to claim 33, wherein the raster scanning magnets (7, 8) are controlled by way of scanner magnet current power supply units for horizontal and vertical correction by control and read-out modules (SAMS) for the raster scanning magnets (7, 8).

36. Method according to claim 33, wherein location measurement is registered and evaluated using a multiwire proportional chamber (16, 17) by way of a location measurement, control and read-out module (SAMO), information stored in the location measurement, control and read-out module (SAMO) of a supervisory control system relating to the desired position of an irradiation plan being compared, for the purpose of transverse compensation, with the measured actual position of the beam position from the location-sensitive detector in real time taking into account the detected transverse movement component of the target volume (1).

37. Method according to claim 33, wherein, by means of the scanner magnet power supply units of the raster scanning apparatus (3), location correction transversely in the X and Y direction and, by means of the depth modulator (6), longitudinal depth correction are carried out from beam position to beam position.

38. Method according to claim 33, wherein fast shut-down of the beam is initiated by the location measurement, control and read-out module (SAMO) of the location-sensitive detector in real time and/or by the movement measurement, control and read-out module (SAMB) of the depth modulator (6), if the difference between a measured value and a desired value of the transverse beam position and/or of the longitudinal depth of penetration w exceeds a threshold that can be set in the realtime software of the control and read-out modules SAMO and/or SAMB.

* * * * *